United States Patent [19]

Lunte et al.

[11] Patent Number: 5,169,510
[45] Date of Patent: Dec. 8, 1992

[54] ION-PERMEABLE POLYMER JOINT FOR USE IN CAPILLARY ELECTROPHORESIS

[75] Inventors: Susan M. Lunte; Craig E. Lunte, both of Lawrence, Kans.; Tommy J. O'Shea, Dublin, Ireland

[73] Assignee: Oread Laboratories, Lawrence, Kans.

[21] Appl. No.: 844,762

[22] Filed: Mar. 2, 1992

[51] Int. Cl.$^5$ .................... G01N 27/26; B01D 57/02
[52] U.S. Cl. .................... 204/299 R; 204/301; 204/180.1
[58] Field of Search ............ 204/299 R, 301, 180.1, 204/183.3

[56] References Cited

U.S. PATENT DOCUMENTS 4,908,116 3/1990 Zare et al. .................... 204/299 R
5,045,172 9/1991 Guzman .................... 204/299 R

OTHER PUBLICATIONS

Thomas J. O'Shea et al "Capillary electrophoresis with electrochemical detection employing an on-line Nafion joint" Journal of Chromatography, 593 (1972) 305-312.

Primary Examiner—John Niebling
Assistant Examiner—John S. Starsiak, Jr.
Attorney, Agent, or Firm—Hovey, Williams, Timmons & Collins

[57] ABSTRACT

Improved capillary electrophoresis (CE) apparatus (10) is provided which includes an intermediate grounding joint (34) serving to isolate delicate electrochemical detectors (32, 54, 58) from the high voltage CE power supply (20). The joint (34) includes a fracture (36) close to the detection end (22) of the apparatus (10) which is covered by a Nafion sleeve (38). The joint (34) is immersed in an ionic buffer reservoir (46) which includes a grounded cathode (48). In fabrication procedures, a capillary tube (12) is scored in proximity to one end (22) thereof, and the Nafion sleeve (38) is slid over the score line. The sleeve (38) is then sealed with epoxy (40, 42) at the ends thereof.

18 Claims, 2 Drawing Sheets

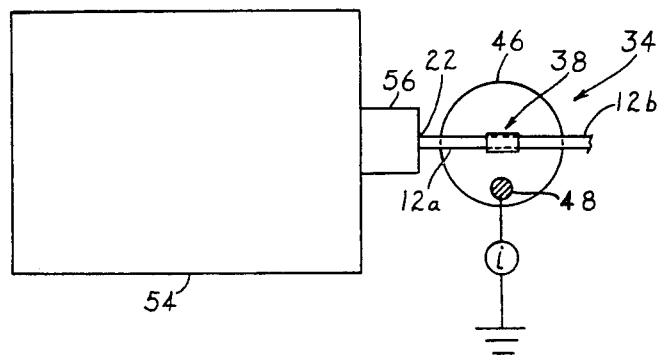
Fig. 4
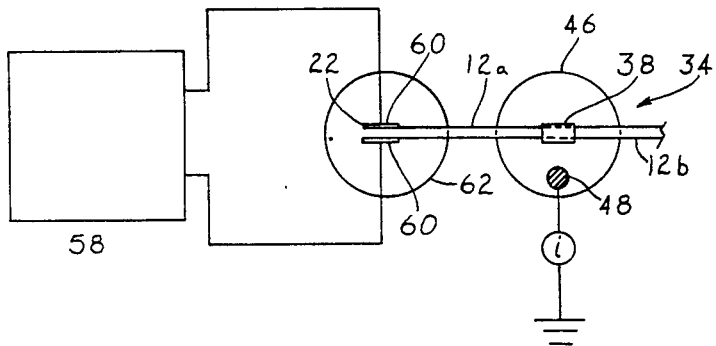
Fig. 5
Fig. 6
Fig. 7
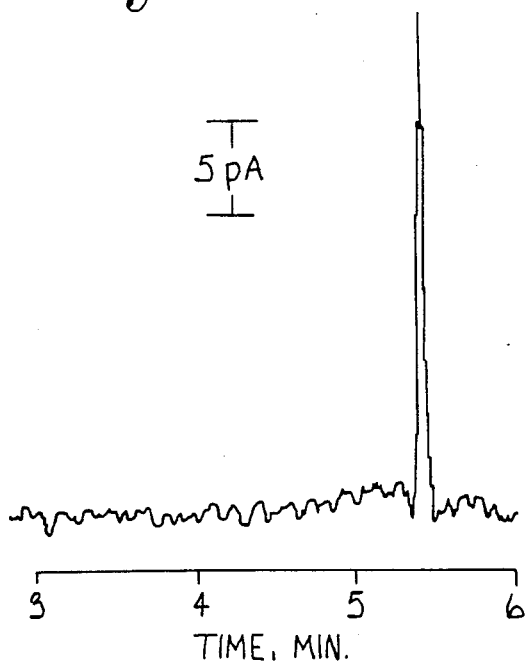
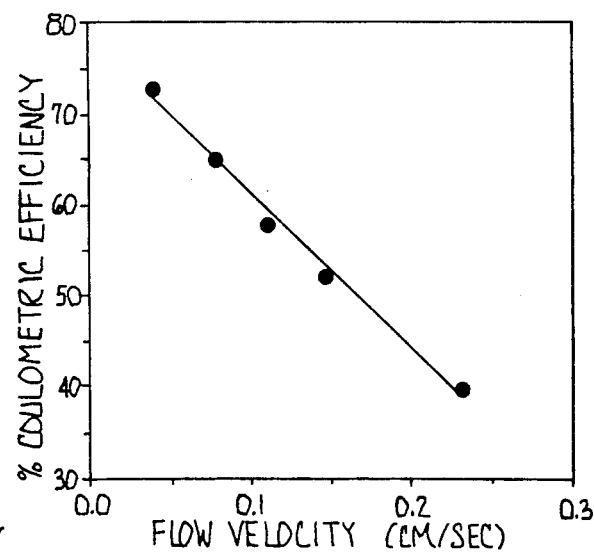

ION-PERMEABLE POLYMER JOINT FOR USE IN CAPILLARY ELECTROPHORESIS

BACKGROUND OF THE INVENTION

1. Field of the Invention

The present invention is broadly concerned with an improved high voltage capillary electrophoretic (CE) apparatus equipped with an easily constructed grounding joint intermediate to the ends of the capillary tube serving to electrically isolate an electrochemical detector from the high voltage applied potential. More particularly, it is concerned with such CE apparatus, and a method of fabricating the ground joint tube assembly thereof, wherein a capillary tube is scored, a flexible, polymeric, ion-permeable sleeve is applied over the score and sealed, and the tube is fractured. The resultant tube assembly gives excellent, reproducible CE results.

2. Description of the Prior Art

Since its introduction over a decade ago, capillary electrophoresis has established itself as a powerful analytical tool for the separation and analysis of complex mixtures (Jorgenson et al., *Anal. Chem.*, 53 (1981) 1298). In CE systems, a fused silica capillary is filled with buffer and a large voltage is applied. By virtue of the presence of ionized silanol groups on the capillary wall, the applied voltage creates electroosmotic flow which allows the charge-independent detection of species injected onto the column. CE capillaries with small diameters is advantageous over conventional slab gel electrophoresis due to higher efficiency, lower joule heating effect and faster analysis times.

One of the main areas of present-day CE research is the development of sensitive detection systems. Because of the small injection volumes involved in CE, high sensitivity/small volume detectors are necessary. UV detection is the most commonly employed detection method for CE. However, since this is an optical technique and is pathlength dependent, the sensitivity is limited when using small diameter capillaries. Laser-based fluorescence detectors are more sensitive, but are expensive and limited to certain wavelengths. Electrochemical detection has an advantage over these methods in that the response is not dependent on pathlength; therefore, very small capillary diameters can be used without sacrifice in signal. It also utilizes relatively inexpensive instrumentation. However, electrochemical detection presents a serious difficulty in that the detection apparatus must be shielded from the high voltage used in the CE separation. If this is not done, the sensitive detection apparatus may be damaged, and very low signal-to-noise ratios will be obtained.

Wallingford and Ewing (*Anal. Chem.*, 53 (1987) 1762; *Anal. Chem.*, 61 (1989) 98) have developed an off-column electrochemical detector, and have reported $10^{-8}$M detection limits for several catechol compounds. In their system, two pieces of capillary column are coupled inside a piece of rigid porous glass capillary. This joint permits the flow of ions but not bulk electrolytic flow, enabling the detection end of the capillary to be held at ground. The fabrication of this joint assembly is quite difficult and intricate. Unless perfect alignment of both sections of capillary is achieved, considerable band broadening can occur. The joint does not appear to be durable as the porous glass is extremely fragile and must be kept submerged in solution. Another limitation of this design is that the porous glass capillary is not readily available. Huang and Zare (*Anal. Chem.*, 62 (1990) 443) designed an on-column frit which also served to isolate the final section of the capillary column from the applied electrical field. However, the authors describe the drawbacks of this design, including lack of capillary-to-capillary reproducibility, leakage of the frit and difficulty of fabrication (requiring the use of a $CO_2$ laser). Recently, Huang et al. (*Anal. Chem.*, 63 (1991) 189) have reported that it is not necessary to isolate the microelectrode from the high voltage if capillaries with very small internal diameter (5 $\mu$m) are employed. In such small capillaries, the current generated by the CE separation is low enough that it does not adversely affect the electrochemical detection. However, as a consequence of the small size, the concentration detection limits are not as low as those reported with larger internal diameter capillary columns.

SUMMARY OF THE INVENTION

The present invention overcomes the problems outlined above and provides a greatly improved CE apparatus which is suited to use with a variety of detectors, particularly, electrochemical detectors of all types. At the same time, the CE apparatus may be readily fabricated.

Broadly speaking, the CE apparatus hereof includes an elongated electrophoretic capillary tube assembly of length (e.g., 1 meter) required for the separation of interest. One end of the tube is designed for connection with a power supply for applying a high voltage across the tube assembly; the opposite end of the tube assembly is adapted for coupling to an appropriate CE detector. The overall apparatus has means for electrically isolating the detector from the applied CE potential, including an opening in the tube assembly intermediate the ends thereof, together with a cover applied over the opening. The opening and cover create a conductive path to ground when the isolating structure is immersed in an ionic bath.

An important feature of the invention resides in the fact that the joint cover is formed of flexible polymeric material which is ion-permeable and of low electrical resistance. Use of such a cover allows easy manufacture and reproducible CE results, and is to be contrasted with prior use of rigid glass bodies which present intractable problems in manufacture.

In preferred forms, the CE tube is initially scored a short distance (e.g., up to 5 cm) from the detection end of the tube. Thereupon, a sleeve of Nafion (perfluorosulfonic acid polymer) is applied over the fracture and sealed with epoxy. The tube is then grasped and fractured at the region of the score, in order to create the requisite opening. As will be appreciated, this effectively creates a pair of closely adjacent aligned tube sections which are bridged by the Nafion sleeve. In practice, even though the applied potential is grounded through the joint, the electroosmotic force generated upstream of the joint serves to push buffer and solute bands through the short remaining section of capillary tube to the detector.

BRIEF DESCRIPTION OF THE DRAWINGS

FIG. 4 is a representation similar to that of FIG. 3, but showing use of a mass spectrometer as the detector;

FIG. 5 is a representation similar to that of FIG. 3, but showing use of a conductance meter as the detector;

FIG. 6 is an electropherogram obtained using the apparatus of FIG. 1, using $7 \times 10^{-8}$M hydroquinone as the analyte; and FIG. 7 is a graph showing the coulometric efficiency of the CE apparatus depicted in FIG. 1 as a function of flow velocity.

DETAILED DESCRIPTION OF THE PREFERRED EMBODIMENTS

Figure 1:
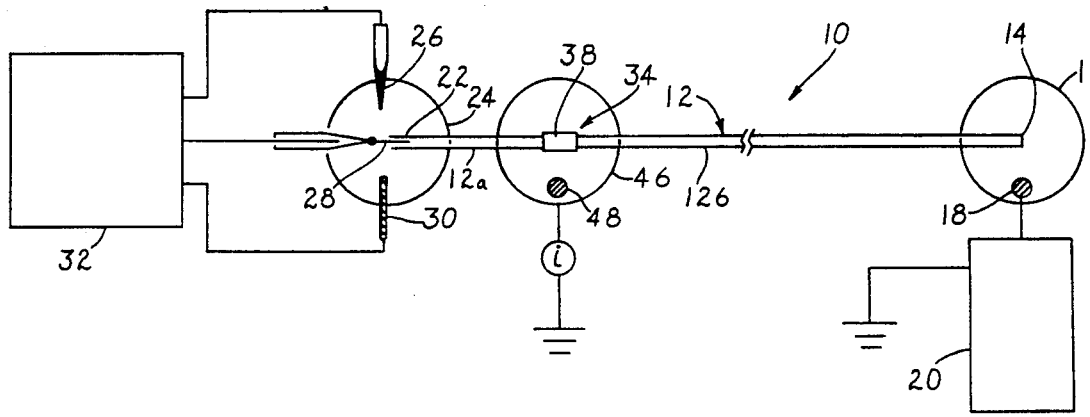
FIG. 1 is a schematic representation of the complete capillary electrophoresis apparatus in accordance with the invention.

Turning first to the drawings, CE apparatus 10 is schematically illustrated in FIG. 1. The apparatus 10 broadly includes an elongated electrophoretic capillary tube assembly 12 having one end 14 thereof immersed in a buffer reservoir 16 equipped with anode 18. The latter is connected with a high voltage power supply 20. The opposite end 22 of the tube assembly is immersed in a detection cell 24 having reference electrode 26, carbon fiber microelectrode 28 and auxiliary electrode 30. The electrodes 26-30 are conventionally connected with amperometric detector 32.

A joint 34 is provided in close proximity to end 22. The joint 34 in tube assembly 12 includes a break or fracture line 36, serving to create opposed tube sections 12a, 12b, and a Nafion sleeve 38 covering line 36 and bridging the tube sections. The opposed ends of the sleeve 38 are sealed with respective epoxy beads 40, 42 as shown. Also, an external reinforcing plate 44 is secured to the joint via beads 40, 42 to provide additional mechanical support. The joint 34 is immersed in buffer reservoir 46 equipped with a grounded cathode 48.

Figure 3:
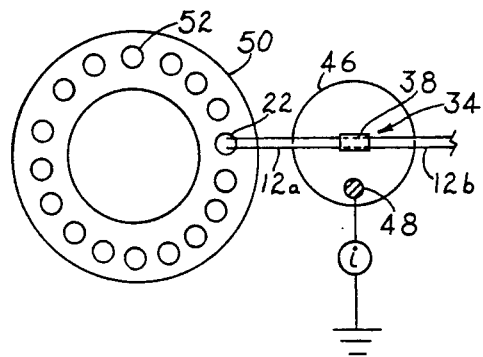
FIG. 3 is a fragmentary schematic representation showing the CE apparatus of FIG. 1, but illustrating use of a rotatable turret-type sample collector at the detection end of the tube assembly.

FIGS. 4-5 depict the use of different detectors, whereas FIG. 3 illustrates a turret-type fraction collector 50 having a plurality of individual collection vials 52 therein. This apparatus may be used to individually collect separated species exiting from end 22. FIG. 4 shows a conventional mass spectrometer 54 and interface 56 operatively coupled to detection end 22. Finally, FIG. 5 illustrates use of conductimetric detection, involving a conductance meter 58 coupled to a pair of spaced electrodes 60 receiving end 22, with the latter immersed in conductivity cell 62.

The following example sets forth a preferred implementation and use of the present invention. It is to be understood, however, that the example is presented for purposes of illustration only, and nothing therein should be taken as a limitation upon the overall scope of the invention.

EXAMPLE

CE Apparatus Preparation

Figure 2:
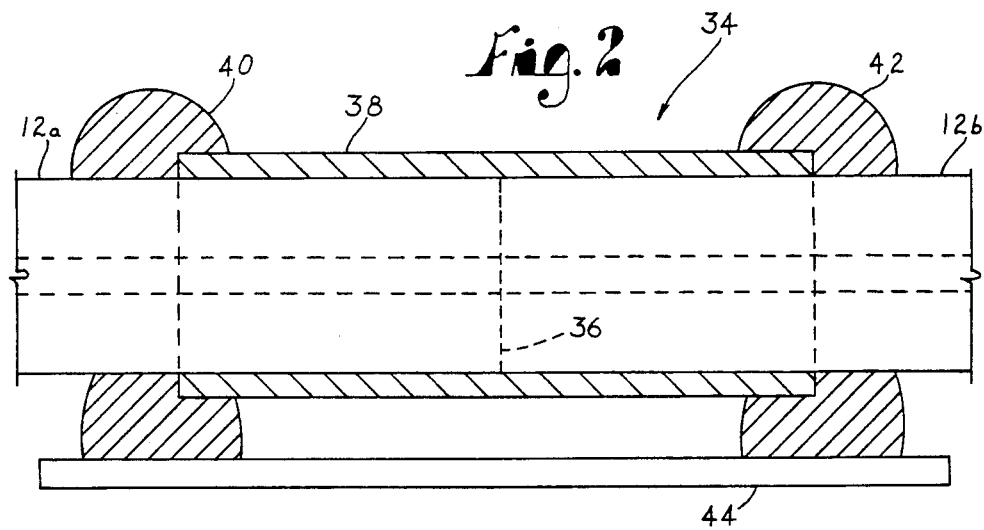
FIG. 2 is a greatly enlarged, sectional view illustrating the construction of the ion-permeable grounding joint forming a part of the FIG. 1 apparatus.

A fused silica capillary (65-70 cm) with an i.d. of 50 µm and an o.d. of 360 µm was obtained from Polymicro Technologies (Phoenix, Ariz.). A capillary cutter (Supelco, Bellfonte, Pa.) was used to score the polyimide coating approximately 1.5 cm from the end of the capillary column. A 1 cm length of Nafion tubing (i.d. 0.33 mm, o.d., 0.51 mm, commercialized as Nafion 1100EW and sold in the hydrogen ion form by Perma Pure Products, Tom's River, N.J.) was then carefully threaded over the score mark. Both ends of the Nafion tubing were then sealed to the capillary tubing using 815 epoxy resin (Mid-Con Plastics, Wichita, Kans.) with 20% (v/v) triethylenetetramine. This was cured overnight. Once cured, gentle pressure was applied to either end of the Nafion tubing causing the capillary to fracture at the score. The Nafion tube held the capillary joint securely in place and insured correct alignment. For additional support, the joint was epoxied to a small section of glass. The resulting construction is depicted in FIG. 2, and the fabrication technique has been repeated with a 100% success rate.

The end of the completed capillary tube remote from the Nafion joint was coupled with a high-voltage dc (0-30 kV) power supply (Glassman High voltage, Inc., Whitehouse Station, N.J.). The anodic high-voltage end of the capillary was isolated in a plexiglas box fitted with an interlock for operator safety. A digital microampere current meter was positioned between a platinum wire ground cathode and ground. Experiments were performed at ambient air temperature (24° C.). For comparative UV work, a $CV^4$ absorbance detector (ISCO, Lincoln, Nebr.) was employed. Sample introduction was performed using pressure (5-10 psi $N_2$) injection, which was found to be reproducible and avoided bias associated with electrokinetic injection. The injection volume was calculated in a continuous fill mode by recording the time required for the sample to reach the detector.

The Nafion joint was manipulated through two openings in opposite sides of a plastic beaker and subsequently sealed in place with epoxy. The joint was immersed in buffer solution and this assembly served as the cathodic buffer reservoir. The detection capillary section was then inserted into the electrochemical detection cell. An illustration of the complete system is shown in FIG. 1.

Previous investigations by Wallingford and Ewing reported that back pressure in the detection capillary section is a significant contributor to zone broadening. However, they demonstrated that if the length is shorter than 2 cm, peak distortion is negligible. Accordingly, the Nafion joint was positioned approximately 1.5 cm from the detection end of the column. A small section of polyimide was removed from the end of the detection capillary to provide better visualization of the insertion of the microelectrode.

The electrochemical detection cell was similar in design to those described previously (Wallingford et al., Anal. Chem., 59 (1987) 1762; Knecht et al., Anal. Chem., 56 (1984) 479). Cylindrical carbon fiber microelectrodes were constructed by aspiration of a 33 µm diameter fiber (Avco Specialty Products, Lowell, Mass.) into a 1.0 mm i.d. capillary tube. The capillary tube was then pulled with a List-Medical Model 3A vertical pipet puller (Medical Systems, Greenvale, N.Y.). Silicone rubber adhesive (General Electric, Waterford, N.Y.) was applied to the tip of the capillary where the fiber protruded. Once cured, the sealant formed an intact seal around the fiber which was found to be resistant to all buffer solutions used. In addition, due to the nature of the sealant, added flexibility was imparted to the fiber, which aided in the insertion of the fiber into the capillary column. The fiber was then cut to the required length, 150-250 µm, using surgical scissors. Electrical contact was established via a copper wire cemented to the carbon fiber using silver epoxy (Ted Pella Inc., Redding, Calif.).

The microelectrode was then mounted onto an X-Y-Z micromanipulator (Newport Corp., Fountain Valley, Calif.) and positioned into the electrochemical detection cell. With the aid of an optical microscope, the microelectrode was aligned and inserted into the capillary column. The cell was operated in a three electrode configuration, with a platinum wire and a laboratory-built Ag/AgCl serving as the auxiliary and reference electrodes, respectively.

Electrode connections were made to the BAS LC-4C (Bioanalytical Systems, West Lafayette, Ind.) amperometric detector. The low currents generated at the microelectrode required the electrochemical cell to be shielded in a Faraday cage to reduce noise contributions from external sources.

Electrochemical pretreatment of the microelectrode was performed using a 50 Hz square-wave waveform of a 2 V amplitude for 1 minute. This was accomplished using a function generator (Exact Electronics Inc., Hillsboro, Oreg.) connected to the external input of the BAS LC-4C. An oscilloscope was used to monitor the applied waveform. Using this arrangement, pretreatment could be performed without removing the microelectrode from the capillary column.

Standard Chemicals

Hydroquinone, glutamic acid, aspartic acid, p-chlorogenic acid, caffeic acid, p-coumaric acid and sinapic acid were purchased from Sigma (St. Louis, Mo.) and used as received. Naphthalene-2-3 dicarboxaldehyde was supplied by Oread Laboratories (Lawrence, Kans.). Sodium cyanide was obtained from Fisher Scientific (Fair Lawn, N.J.).

All other chemicals were analytical reagent grade. All solutions were prepared in NANOpure water (Sybron-Barnstead, Boston, Mass.) and filtered through a 0.45 $\mu$m pore size membrane filter before use.

Apple Juice Preparation

The phenolic acids present in apple juice (Tree Top Inc., Selah, Wash.) were separated from possible interferants by passing 4 mL of juice through a Sep-Pak $C_{18}$ cartridge and washing the column with 10 mL of NANOpure water. A 2 mL volume of 0.01M sodium borate solution (pH 9.25) was used to elute the phenolic acids. Neutral phenols remained on the column. This extract was directly injected into the capillary.

Brain Homogenate Preparation

A rat was sacrificed by cervical dislocation and the brain removed. Approximately 1.7 g of brain was homogenized in 10 mL of 50 mM borate buffer, pH 9.0, for 15 minutes. One mL of homogenate was then removed and acidified with 80 $\mu$L of concentrated perchloric acid and centrifuged at 13,000 rpm for 10 minutes. The supernatant was filtered with a 2 $\mu$m filter. A 50 $\mu$L aliquot of the supernatant was derivatized in a final volume of 1 mL. The derivatizing procedure was carried out as previously described (de Montigny et al., *Anal Chem.*, 59 (1987) 1096).

Results

Several tests were performed to evaluate the Nafion joint and to characterize its performance. No substantial difference (<1%) in the current measurement was observed between capillaries that did not contain the joint and those that had been modified when the same applied field strength and buffer were used.

No difference in electroosmotic flow was obtained when grounding was conducted either through the joint or at the detection end of the capillary column. As this experiment could not be carried out with the electrochemical detector, a UV-VIS detector was employed. Current measurements taken at both of these grounded positions were essentially the same. Reproducibility of joint-to-joint construction was examined based on the measure of electroosmotic flow for six modified columns. The percent relative standard deviation was calculated to be 6.8%. No deterioration of the operation of a modified column was apparent following daily use over a two-month period.

Although the Nafion joint completed the electrical circuit, the detection end of the column does not appear to be at "true" ground, as noise levels were found to be proportional to the applied voltage. Furthermore, when buffers were used that exhibited higher electrophoretic currents (i.e., buffers of a lower resistance), detector noise was observed to increase. This phenomenon has also been reported previously. In order to minimize this effect, buffers of high resistance should be employed.

To ascertain the detector response using the described system, hydroquinone was chosen as the test analyte. Using 0.01M sodium acetate buffer (pH 6.0) and a separation voltage of 425 V cm$^{-1}$, linear regression analysis for concentrations ranging from $7\times10^{-8}$M to $1\times10^{-4}$M provided a calibration curve with a correlation coefficient of 0.998 (n=10). The high separation efficiency achievable with CE was apparent, with the number of theoretical plates calculated from the peak half-width for hydroquinone being in the order of 185,000. The detection limit for this compound was calculated from the electropherogram shown in FIG. 6 and was determined to be $6\times10^{-9}$M based on S/N=2. Using 5.8 nL as the injection volume, the detection limit corresponds to 34.8 amol. From a review of literature, this is the lowest concentration limit of detection reported using CE with electrochemical detection. Percent relative standard deviations for the reproducibility of migration time and the detector response for hydroquinone were 0.7% and 1.8%, respectively (n=8).

The coulometric efficiency of the detector was also examined. Insertion of a 33 $\mu$m o.d. carbon fiber into a 50 $\mu$m i.d. capillary produces an annular flow width of approximately 8.5 $\mu$m. This, and the high sensitivity, are indicative of a thin-layer flow cell of high coulometric efficiency. To measure the coulometric efficiency as a function of flow velocity, a known volume of $1\times10^{-4}$M hydroquinone was injected. Different flow velocities were achieved by adjustment of the applied electrophoretic voltage between 65 V/cm and 400 V/cm. The coulometric efficiency could be determined by knowing the number of moles, current sensitivity, and chart speed, and that the oxidation of hydroquinone involves 2 faradays/mole. The coulometric efficiency was determined at several flow rates. FIG. 7 illustrates the data obtained in this study and, as expected, demonstrates the high efficiencies for flow velocities typically utilized in CE separations.

The application of this system to apple juice sample matrices was examined. Based on migration times, three separate peaks A, B and C were identified as chlorogenic acid, p-coumaric acid, and caffeic acid, respectively. However, migration time is not always a reliable indicator of peak identity, particularly in CE where the sample matrix can have a considerable effect on the mobility of the sample constituents. For further verification of peak identity/purity assessment, voltammetric characterization was utilized. The combination of voltammetric characterization and migration time provided peak identity assignments with a high degree of certainty.

It has been shown that it is not necessary to obtain the entire voltammogram of the analyte in order to characterize sample components; the comparison of current response in the region where it changes most rapidly is sufficient (Roston et al. *Anal. Chem.*, 53 (1981) 1695). To do this, the current response obtained at a potential near $E_{\frac{1}{2}}$ (where the current is most dependent on potential) was ratioed to the current response at a potential where the current was no longer dependent on potential (mass transport-limited value). Since each phenolic acid has a different hydrodynamic response curve in terms of voltage and shape, the ratio is unique to each compound. Current ratios have previously been employed extensively for voltammetric characterization of compounds in complex samples (Lunte et al., *Analyst* 113 (1988) 99; Roston et al. *Anal. Chem.*, 54 (1982) 1417A; Lunte et al. *Anal. Chem.*, 55 (1983) 1458). In this system, the current responses for both standards and sample peaks were measured at 500, 750 and 950 mV. Current ratios (ratioed to 950 mV) recorded are given in Table 1. The ratios for p-coumaric acid and caffeic acid were virtually identical to those of the sample components eluting at the same time. However, Peak A and chlorogenic acid did not exhibit similar voltammetric behavior, indicating impurity. This was further verified when sinaptic acid, another phenolic constituent of apple juice, was found to co-elute with chlorogenic acid.

TABLE 1

| Voltammetric Characterization of Apple Juice Components | | | | | | |
|---|---|---|---|---|---|---|
| | Retention Time (minutes) | | 550 mV/ 950 mV | | 750 mV/ 950 mV | |
| Sample Components | Sample | Standard | Sample | Standard | Sample | Standard |
| Chlorogenic acid | 8.0 | 8.0 | 0.011 | 0.053 | 0.171 | 0.263 |
| p-Coumaric acid | 9.1 | 9.0 | 0.025 | 0.026 | 0.254 | 0.246 |
| Caffeic acid | 10.5 | 10.4 | 0.313 | 0.306 | 0.543 | 0.523 |

The detection of glutamic and aspartic acid in a rat brain homogenate was also investigated. These are important excitatory amino acids that can play a role as neurotransmitters in the brain. Both amino acids lack electrochemically active moieties; therefore, derivatization is necessary for their detection. Naphthalenedialdehyde reacts with primary amines in the presence of cyanide to produce cyano[f]benzoisoindole (CBI) derivatives. These have been shown to be electroactive at moderate oxidation potentials. Electropherograms of a standard mixture of $1 \times 10^{-5}$M of both CBI-amino acids were generated, and for the derivatized brain tissue homogenate in which both glutamic and aspartic acid were detected. This is the first reported use of a derivatizing agent to enhance detection in CE with amperometric detection.

It was found that the carbon fiber had to be pretreated between successive injections of brain homogenate samples in order to maintain current sensitivity. It is presumed that fouling of the electrode surface occurs due to the formation of insoluble reaction products and the pretreatment "cleans" these from the surface. Electrochemical pretreatment has been shown previously to have a dramatic effect on the response of carbon fiber microelectrodes. Application of a square-wave waveform to the microelectrode increased the current sensitivity nearly tenfold over that of the untreated electrode. The detector response was also found to be very reproducible when the electrode was pretreated between injections.

We claim:

1. A method of producing a capillary electrophoresis grounding joint, comprising the steps of:
    providing an elongated electrophoretic capillary tube;
    scoring said tube at a region thereof intermediate the ends thereof;
    placing a sleeve of ion-permeable material over said score region; and
    fracturing said tube at said score region.

2. The method of claim 1, including the step of sealing the opposed ends of said sleeve to said tube, prior to said fracturing step.

3. The method of claim 2, said sealing step comprising applying epoxy resin to the ends of said sleeve.

4. The method of claim 1, said sleeve being formed of material which has sufficient flexibility to permit manual manipulation of said tube to create said fracture.

5. The method of claim 1, said sleeve being formed of a material selected from the group consisting of the polymers of perfluorosulfonic acid, perfluorocarboxylate, perfluorophosphate, perfluorosulfamide, perfluorosulfonate/carbonate, cellulose acetate, and mixtures thereof.

6. Capillary electrophoresis apparatus comprising:
    an elongated electrophoretic capillary tube assembly presenting a pair of opposed ends respectively adapted for operative connection with detecting means and a power supply for applying a high voltage potential across the tube assembly; and
    means for electrically isolating said detecting means from said applied potential, including structure defining an opening in said tube assembly intermediate said ends thereof, and a cover applied to said tube assembly in covering relationship to said opening,
    said opening and cover being cooperable for creating an electrically conductive path to ground when the isolating means is immersed in a grounded ionic bath,
    said cover being formed of flexible polymeric material which is ion-permeable and of low electrical resistance.

7. The apparatus of claim 6, said opening-defining structure comprising a line of fracture whereby the tube assembly includes a pair of closely adjacent, aligned tube sections.

8. The apparatus of claim 6, said cover being a sleeve.

9. The apparatus of claim 8, including means for sealing the opposed ends of said sleeve to said tube assembly.

10. The apparatus of claim 9, said sealing means comprising epoxy resin.

11. The apparatus of claim 6, said cover being formed of a material selected from the group consisting of the polymers of perfluorosulfonic acid, perfluorocarboxylate, perfluorophosphate, perfluorosulfamide, perfluorosulfonate/carbonate, cellulose acetate, and mixtures thereof.

12. Capillary electrophoresis apparatus, comprising:
    elongated electrophoretic capillary tube assembly presenting a pair of opposed ends;

a power supply operatively coupled with one of said ends for applying a high voltage across the tube assembly;

electrophoretic detection means operably coupled with the opposed end of said tube assembly; and means for electrically isolating said detecting means from said applied potential, including structure defining an opening in said tube assembly intermediate said ends thereof, and a cover applied to said tube assembly in covering relationship to said opening, said opening and cover being cooperable for creating an electrically conductive path to ground when the isolating means is immersed in a grounded ionic bath, said cover being formed of flexible polymeric material which is ion-permeable and of low electrical resistance.

13. The apparatus of claim 12, said detection means being selected from the group consisting of amperometric, conductimetric, and mass spectrometric detectors.

14. The apparatus of claim 12, said detection means comprising individual species collection means.

15. The apparatus of claim 12, said opening-defining structure comprising a line of fracture whereby the tube assembly includes a pair of closely adjacent, aligned tube sections.

16. The apparatus of claim 15, said cover being a sleeve.

17. The apparatus of claim 16, including means for sealing the opposed ends of said sleeve to said tube assembly.

18. The apparatus of claim 12, said cover being formed of a material selected from the group consisting of the polymers of perfluorosulfonic acid, perfluorocarboxylate, perfluorophosphate, perfluorosulfamide, perfluorosulfonate/carbonate, cellulose acetate, and mixtures thereof.

* * * * *